US007935938B2

(12) United States Patent
Thabeth et al.

(10) Patent No.: US 7,935,938 B2
(45) Date of Patent: May 3, 2011

(54) APPARATUS FOR MEASURING FLUORESCENT MATERIAL IN A LIQUID

(75) Inventors: Khalid Thabeth, Newtownabbey (GB); Frank Lunney, Belfast (GB); Turan Mirza, Lisburn (GB)

(73) Assignee: Advanced Sensors Limited, Carrickfergus (GB)

( * ) Notice: Subject to any disclaimer, the term of this patent is extended or adjusted under 35 U.S.C. 154(b) by 188 days.

(21) Appl. No.: 12/280,375

(22) PCT Filed: Feb. 23, 2007

(86) PCT No.: PCT/EP2007/001581
§ 371 (c)(1),
(2), (4) Date: Aug. 22, 2008

(87) PCT Pub. No.: WO2007/096179
PCT Pub. Date: Aug. 30, 2007

(65) Prior Publication Data

US 2009/0032733 A1 Feb. 5, 2009

(30) Foreign Application Priority Data

Feb. 23, 2006 (GB) .................................. 0603636.2

(51) Int. Cl.
*G01J 1/58* (2006.01)
(52) U.S. Cl. .................................................... 250/458.1
(58) Field of Classification Search ................ 250/458.1
See application file for complete search history.

(56) References Cited

U.S. PATENT DOCUMENTS 4,034,219 A * 7/1977 Louden et al. ................ 250/301
4,797,550 A 1/1989 Nelson et al.
4,835,384 A * 5/1989 Jones et al. .................. 250/226
5,381,002 A 1/1995 Morrow et al.
5,541,468 A * 7/1996 Frey et al. ..................... 310/334
6,324,900 B1 * 12/2001 Bruno et al. ................. 73/61.48
2002/0131139 A1 * 9/2002 Mandella et al. ............. 359/215
2005/0088646 A1 4/2005 Kong et al.
2007/0077178 A1 * 4/2007 Wagner ...................... 422/82.08
2009/0294691 A1 * 12/2009 Trinquet et al. ............ 250/459.1

FOREIGN PATENT DOCUMENTS

GB 2 336 668 A 10/1999
WO WO 2006010839 A2 * 2/2006

* cited by examiner

*Primary Examiner* — David P Porta
*Assistant Examiner* — Shun Lee
(74) *Attorney, Agent, or Firm* — Porter, Wright, Morris & Arthur, LLP

(57) ABSTRACT

An apparatus (10) for measuring, in particular, the amount of oil present in a quantity of water. The apparatus comprises a measurement chamber (12) having an optical window (18) through which an excitation signal may be transmitted and fluorescent light may be detected. The apparatus further includes an ultrasonic transducer (34) coupled to the measurement chamber and having a pair of channels (44,45) formed therein, the channels opening onto the measurement window (18). A respective light guide (28) is inserted into each channel, one light guide being arranged to deliver the excitation signal into the chamber through the measurement window, the other being arranged to carry fluorescent light from the chamber.

19 Claims, 8 Drawing Sheets

Water Flow
Water Flow
PC & Display Module 70
RS232
Ethernet
4-20mA
Valve 1
Valve 2
4-20mA
RS232
30
Signal Processing/ Conditioning
68
DAC & PC Interface Board
Valve Control Interface
Ultrasonic PSU 50
Ultrasonic PSU Control
Laser Drive 62
Mains Supply Conditioning
36
40

APPARATUS FOR MEASURING FLUORESCENT MATERIAL IN A LIQUID

FIELD OF THE INVENTION

The present invention relates to an apparatus for measuring fluorescent material in a liquid. The invention relates particularly, but not exclusively, to the measurement of oil in a liquid, particularly water.

BACKGROUND TO THE INVENTION

There are many applications that require measurement of the quantity of oil that is present in a liquid. For example, in pipes leading from oil production or refining facilities it may be required to measure the amount of oil that is present in the liquid (mainly water) flowing in the pipes. To this end it is known to provide an in-line measurement apparatus which measures the amount of oil that is present.

Oil has a natural fluorescence and so, commonly, such measurement apparatus measure the quantity of oil by the detection of fluorescence. Apparatus that detect and/or measure fluorescence are commonly referred to as fluorometers. A fluorometer usually includes a light source for causing fluorescence in a target substance and a detector for measuring the resultant fluorescence.

A typical in-line fluorometer has a measurement window through which the excitation light source is transmitted into a measurement region and through which the resultant fluorescent light is received by the fluorometer. One problem with such fluorometers is the fouling of the measurement window by substances within the measurement region. This problem may be addressed by using an ultrasonic device to clean the window. The ultrasonic device may also be used to agitate the liquid/oil under measurement and this helps to create, by emulsification and homogenisation, a consistent particle or droplet size for the suspended oil which in turn facilitates consistent measurement of fluorescence.

Conventional in-line fluorometers suffer from a variety of problems that impair their performance, including poor efficiency resulting from losses in the optical circuit, and the turbidity of liquid being measured.

It would be desirable, therefore, to provide an improved apparatus for measuring fluorescent material in a liquid.

SUMMARY OF THE INVENTION

The invention relates to an apparatus for measuring the amount of fluorescent material in a liquid, the apparatus comprising a measurement chamber having an optical window through which an excitation signal may be transmitted and fluorescent light may be detected; an excitation source for generating said excitation signal and a detector for receiving said fluorescent light.

Apparatus embodying the invention are typically connected in-line with a pipe or conduit which carries a liquid, e.g. water, and a second substance, e.g. oil, which may be naturally fluorescent (e.g. hydrocarbon substances such as oil) or which are treated with a fluorescent agent, or tracer, such as fluorescein. The apparatus is able to measure the quantity of the second substance by exciting the fluorescent material and measuring the resulting fluorescence.

From a first aspect, the invention is characterised by the provision of an ultrasonic transducer coupled to the measurement chamber and having first and second channels formed therein, wherein a respective light guide is at least partially inserted into one or both of said channels, the or each light guide either being part of, or associated with, the excitation source and being arranged to deliver the excitation signal into the chamber through the measurement window, or being part of, or associated with, the detector and being arranged to carry fluorescent light from the chamber. Alternatively, or in addition, the excitation source, especially a laser source, may be at least partially inserted into one of said channels and arranged to deliver the excitation signal into the chamber through the measurement window.

The channels are typically non-parallel and converge in a direction towards the window. In the preferred embodiment, the channels are formed in a coupling mass portion of the ultrasonic transducer, the coupling mass being held in contact with the outer face of the measurement window in order to impart ultrasonic vibrations thereto. The channels are preferably formed in a first portion of the coupling mass. The measurement window is preferably held or clamped between the first portion of the coupling mass and a second portion of the coupling mass. The second portion conveniently forms at least part of a wall of the measuring chamber.

Preferably, a respective protective sleeve is provided between the light guide/excitation source and the wall of the respective channel, the sleeves typically being inserted into a respective channel.

From a second aspect, the invention is characterised by arrangement of the excitation source and detector to focus on a target region at, or close to, the face of the measurement window within the chamber. The target region is preferably centred at a point less than 10 mm, preferably less than 5 mm, and more preferably within 2 mm of, the face of the window.

From a third aspect, the invention is characterised by arrangement of the excitation source and the detector such that the line-of-sight of the detector and the excitation signal lie in a common pane which is not perpendicular with the face of the measurement window. The preferred arrangement is such that the line-of-sight and the excitation signal each lie in a respective plane that is perpendicular with the face of the window, each plane being non-coplanar with one another and, preferably, being substantially perpendicular with one another.

From a fourth aspect, the invention is characterised by the provision of a flushing system comprising a source of a cleaning fluid, e.g. clean water, in fluid communication, during use, with an inlet to the chamber; a valve provided between the fluid source and the inlet for controlling the flow of cleaning fluid to the chamber, the valve being controllable, typically by the apparatus itself, to allow a quantity of cleaning liquid to flush the chamber.

Further advantageous aspects of the invention, including methods of measuring the amount of fluorescent material in a liquid and of cleaning the measurement chamber, will be apparent to those ordinarily skilled in the art upon review of the following description of specific embodiments and with reference to the accompanying drawings.

BRIEF DESCRIPTION OF THE DRAWINGS

Embodiments of the invention are now described by way of example and with reference to the accompanying drawings in which.

DETAILED DESCRIPTION OF THE DRAWINGS

Figure 1:
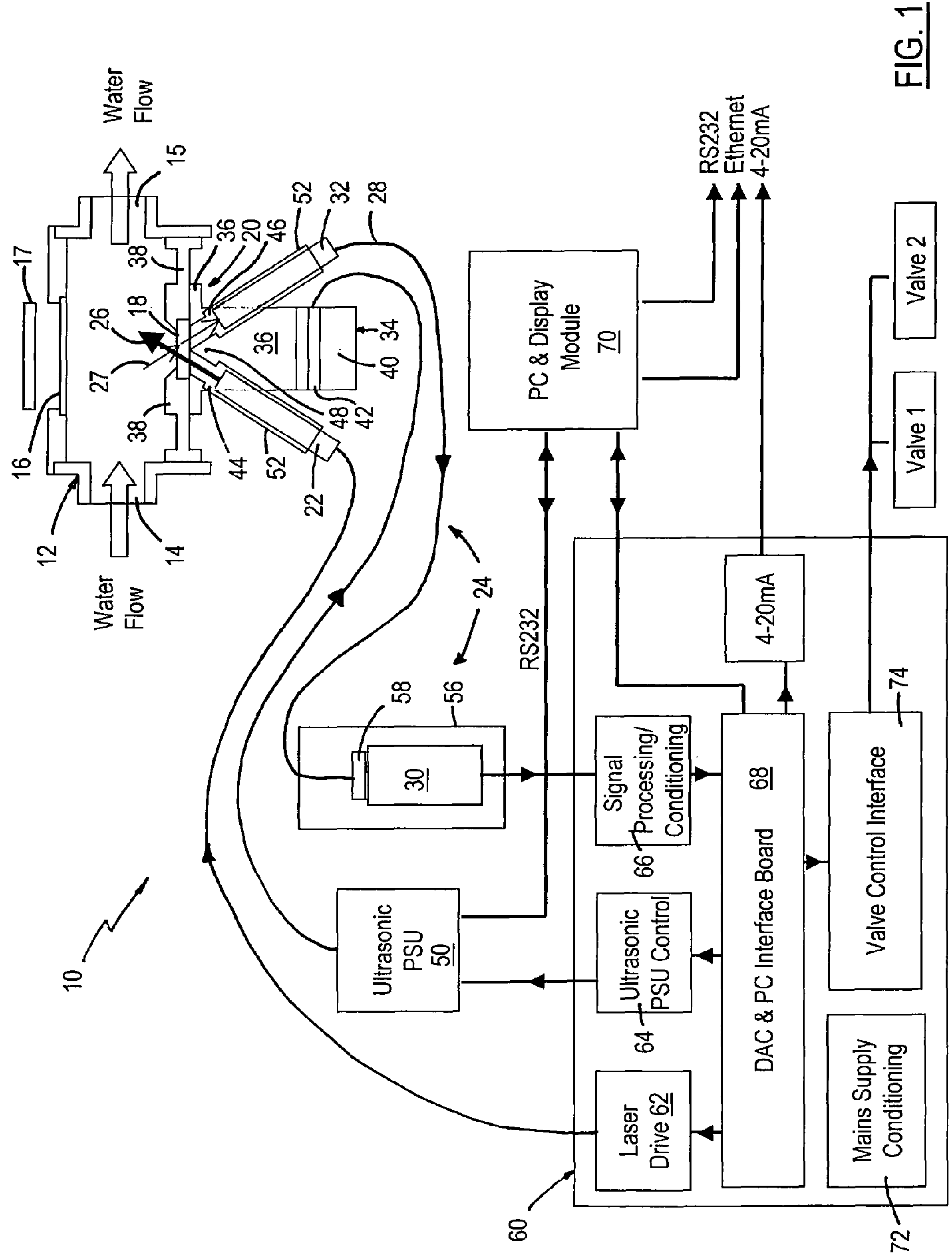
FIG. 1 is a schematic view of an apparatus embodying the invention.

Referring now to FIG. 1 of the drawings, there is shown, generally indicated as 10, an apparatus for measuring fluorescence in a liquid, the apparatus 10 embodying the present invention. The apparatus 10 may also be referred to as a fluorometer. In particular, the apparatus 10 may be said to be an in-line apparatus or fluorometer since it is incorporated, in use, into a pipe or conduit (not shown in FIG. 1) through which a liquid, e.g. water, including a fluorescent material, e.g. oil, flows. In the following description, the liquid is assumed to comprise water and the fluorescent material is assumed to comprise oil, although it will be understood that that the invention is not limited to these. For example, the target substance to be detected may be naturally fluorescent and/or may include an added fluorescent agent such as fluorescein.

The apparatus 10 comprises a measurement chamber 12 which may be provided by a portion of said pipe or conduit or, preferably, by a section of pipe or conduit that is separately formed from the pipe or conduit but is adapted for in-line connection therewith using any suitable conventional connectors (not shown). The chamber 12 includes an inlet 14 through which water may flow into the chamber 12 and an outlet 15 through which water may flow out of the chamber 12. The inlet 14 and outlet 15 are preferably substantially aligned to a common axis, e.g. oppositely disposed on the chamber 12, so that water may flow straight through the chamber 12 in a generally linear fashion.

It is preferred that the chamber 12 includes a viewing window 16 that allows the contents of the chamber 12 to be viewed. The viewing window may be formed from any suitable transparent material, e.g. sapphire crystal or quartz. Preferably, a removable cap 17, e.g. a screw-fit cap, is provided for covering the viewing window 16 and blocking ambient light from the chamber 12.

The chamber 12 also includes a measurement window 18. The measurement window may be formed from any suitable translucent, but advantageously transparent, material which is capable of withstanding ultrasonic shock, e.g. sapphire crystal.

A measurement head assembly 20 is coupled to the chamber 12. The measurement head assembly 20 includes excitation means comprising an excitation source 22 and a detector 24. The excitation source 22 is arranged to direct an excitation signal 26 through the measurement window 18 into the chamber 12 in order to cause fluorescence of the oil mixed with, or suspended in, the water. The detector 24 is arranged to receive or detect said fluorescence through the window 18.

The excitation signal 26 may comprise any signal that causes fluorescence in the target material. Typically, the excitation signal 26 comprises a light signal of any suitable wavelength, including visible light, UV light and IR light. In the present embodiment, the excitation source 22 comprises a laser source, e.g. a 3 mW laser diode module of 405 nm wavelength.

Advantageously, the detector 24 includes a light guide 28 for collecting or receiving fluorescent light from the chamber 12 and guiding it to a photosensor or photodetector module 30. The light guide 28 comprises at least one optical fibre (or other optical conduit), but typically a plurality of optical fibres (or other conduits) packaged together, to provide an optical transmission channel by which light may be directed to the photosensor 30. A light guide may also be referred to as an optical cable and may comprise a bundle of one or more individual optical cables, wires or the like. The free end of the light guide 28 preferably carries an end piece or casing 32 which surrounds the optical fibres while leaving their free ends exposed so that they may collect light.

The apparatus 10 also includes means for imparting vibrations, preferably ultrasonic vibrations, to the window 18. Conveniently, this comprises an ultrasonic transducer 34 comprising, in the preferred embodiment, a front or coupling mass having two portions identified as 36 and 38, a back mass 40 and typically at least two piezoelectric transducers 42 sandwiched between the coupling mass 36 and the back mass 40. The front and back masses may be formed from any suitable material, typically metal. It is preferred that the coupling mass portion 38 is formed from a corrosion resistant material, e.g. stainless steel, to limit the corrosive effects that the water sample in the chamber 12 may otherwise have. The piezoelectric transducers 42 typically comprise ceramic, or piezo-ceramic elements or disks. During use, the ceramic transducers 42 convert electrical energy, supplied by an ultrasonic power supply unit 50, into mechanical energy which is imparted to the coupling and back masses in conventional manner.

The coupling mass portion 36 is shaped to define first and second channels 44, 46 for receiving, in the present embodiment, the laser 22 and the casing 32 respectively. The channels 44, 46 may be formed by, for example, appropriate machining of the coupling mass portion 36. The channels 44, 46 are non-parallel and converge in a direction towards the window 18. The coupling mass portion 36 includes a tip or head 48 (located between the channels 44, 46 when viewed in cross-section as shown in FIG. 1).

The measurement window 18 is held or clamped between the portion 36 of the coupling mass and the portion 38 of the coupling mass. The preferred arrangement is such that the tip or head 48 of the coupling mass portion 36 is held in contact with the outer face of the measurement window 18 in order to impart ultrasonic vibrations thereto. Moreover, the channels 44, 46 open onto the measurement window 18.

The coupling mass portion 38, which may be fixed to the portion 36 by any suitable means, e.g. by bolts (not shown), serves as all or part of a wall of the chamber 12. To this end, the portion 38 of the coupling mass may be fixed to the chamber 12 by any suitable means, e.g. bolts (not shown). The coupling mass portions 36, 38 are ideally held rigidly or substantially rigidly together so that the window 18 is held firmly or substantially rigidly in place. The coupling mass portion 38 may be rigidly, or substantially rigidly, fixed to the chamber 12. Preferably, at least the coupling mass portion 38 is arranged to flex in a diaphragm-like manner in order to accommodate ultrasonic vibrations during use.

The channels 44, 46 are formed in the coupling mass 36 and so form part of the coupling mass. Similarly, the measurement window 18 effectively forms part of the coupling mass since it is held between two portions 36, 38 of the coupling mass.

Providing the laser source 22 in the channel 44 is advantageous since it obviates the need to include an optical guide system to direct the laser light into the measurement chamber 12 and so reduces the complexity of the apparatus 10 and eliminates the losses associated with optical guide systems. Similarly, by placing the free end of the light guide 28 in the channel 46 it is close to (preferably as close as possible to) the measurement window 18 and is therefore able to gather enough light to allow accurate measurements. This obviates the need to provide a more conventional optical guide system (typically including lenses and/or mirrors) for directing light out of the chamber 12 and so eliminates losses associated with such optical guide systems. Placing such components in close proximity with the ultrasonic transducer 34 would not conventionally be considered to be a design option because of the effects that the ultrasonic vibration can have on the components.

In order to protect the components that are, in use, inserted into the channels 44, 46 from the effects of ultrasonic vibration, e.g. ultrasonic shock, it is preferred to provide a respective sleeve 52 between the walls of the channel 44, 46 and the component (the laser 22 or the casing 32/light guide 28 in the present embodiment) inserted therein. The sleeves 52 may be formed from any suitable material and may be rigid, semi-rigid or flexible. It is preferred that the sleeves 52 are formed from plastics, especially acetal plastics as, for example, provided under the trade name DELRIN by DuPont. Acetal, and similar material, provides high strength and resistance to impact and fatigue while having a limited impact on the ultrasonic transducer resonant frequency and dynamic performance.

Figure 4:
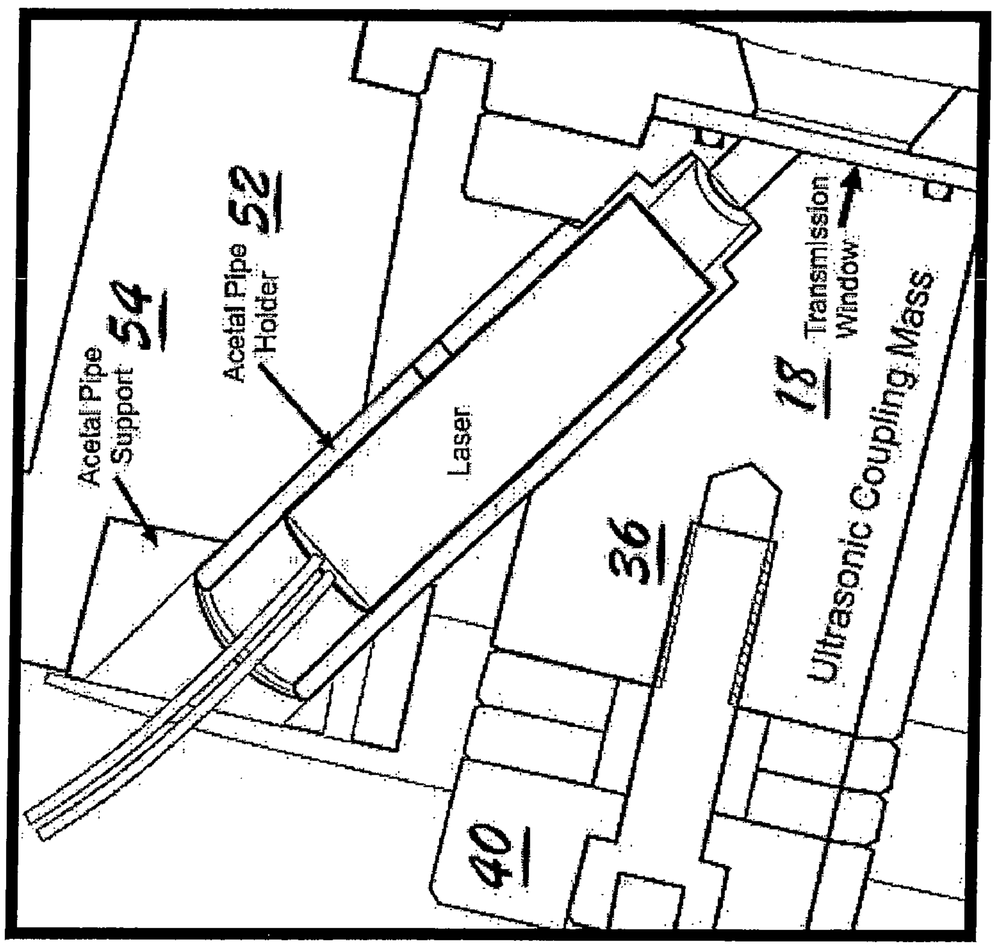
FIG. 4 is a close-up view of part of the apparatus of FIG. 1.

In the preferred embodiment, as best illustrated in FIG. 4, the sleeves 52 (only one shown in FIG. 4) are inserted into the respective channel 44, 46 and are preferably self-retaining therein by means of, for example, a close or friction fit with the wall of the channel 44, 46. The sleeves 52 are preferably removable from the channels 44, 46. Typically, the components being inserted into the channels are longer than the channels and so project therefrom. It is therefore preferred that the sleeves 52 are dimensioned to project from the channels 44, 46. The projecting portion of the sleeve 52 may be supported by a suitable support member 54 (not shown in FIG. 1).

Figure 2:
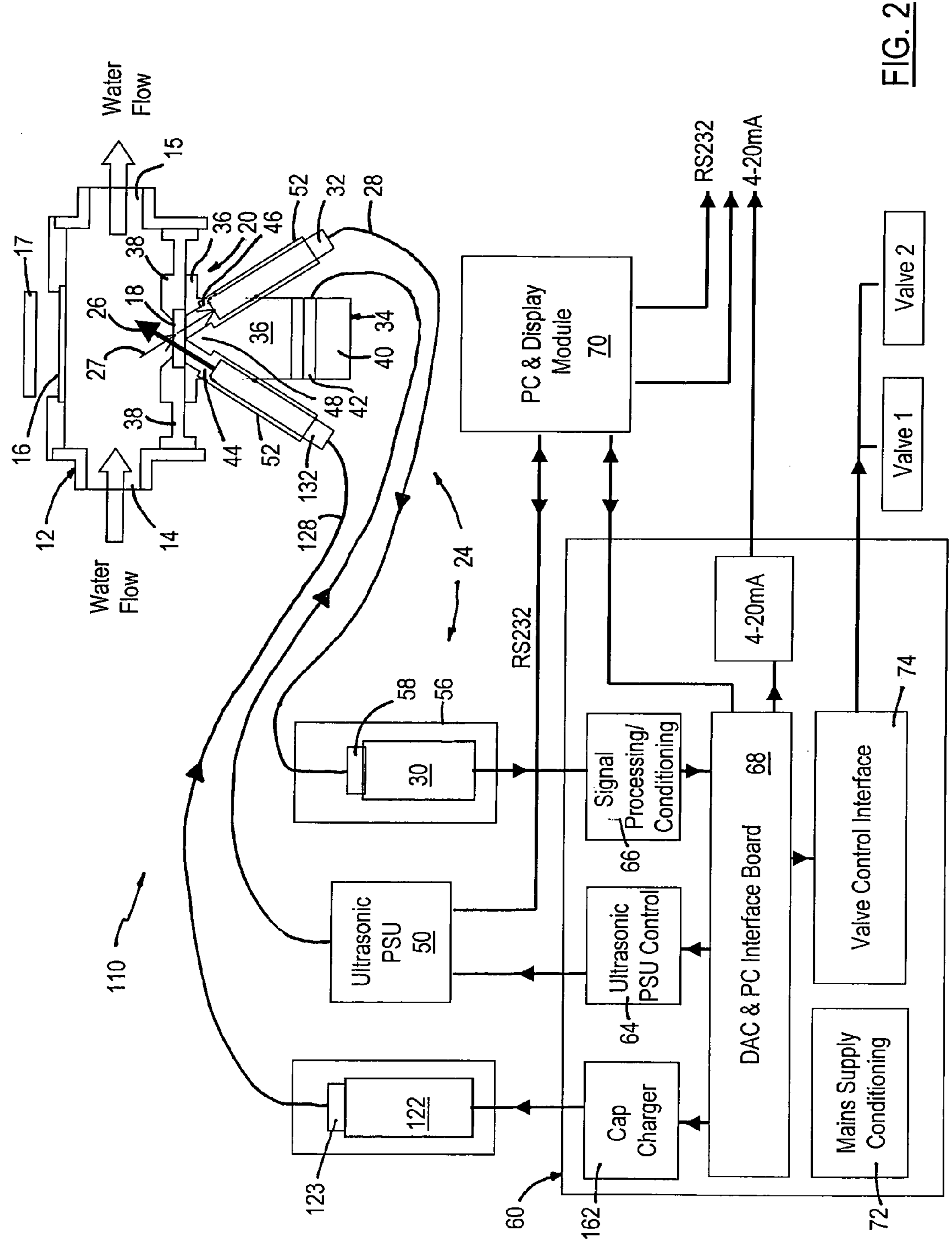
FIG. 2 is a schematic view of an alternative apparatus embodying the invention.

FIG. 2 shows an alternative apparatus 110 which is similar to the apparatus 10 and in which like numerals are used to indicate like parts. In place of the laser 22, the apparatus 110 uses an alternative excitation source in the form of a Xenon lamp 122. The Xenon lamp 122 may be associated with one or more optical filters 123 to produce an excitation light signal in a desired frequency band. The Xenon lamp 122 does not lend itself to being inserted into the channel 44 and so the excitation light is directed from the lamp 122 to the measurement window 18 by means of a light guide 128 which may be similar or identical to the light guide 28. A casing 132 is provided at the free end of the light guide 128 and is inserted into the channel 44 and associated sleeve 52 as is described for the light guide 28. Similarly, in other embodiments (not illustrated) where the excitation source is not suited to being inserted into the channel 44, a light guide may be used.

The detector 24 typically includes, or is associated with, an optical receiver assembly 56 for receiving the detected optical signals via the light guide 28 and converting them into corresponding electrical signals. The conversion from optical to electrical is performed by the photosensor module 30 which may take any suitable conventional form. Advantageously, one or more optical filters 58 are provided to filter the optical signal before reaching the photodetector 30, the filter(s) being selected to pass light within the frequency band of interest. For example, the filter wavelength may typically be 480 nm, but can vary depending on the oil species, or other material being monitored.

The apparatus 10 further includes processing and control circuitry shown in FIG. 1 on a master circuit board 60. The composition and configuration of the circuitry may vary as will be apparent to a skilled person. In the illustrated example, the circuitry includes a laser drive unit 62 for controlling or driving the laser 22, or a cap charger 162 in the embodiment of FIG. 2; a control unit 64 for the ultrasonic power supply unit 50; a signal processing/conditioning unit 66 for processing/conditioning the electrical signals produced by the optical receiver assembly 56; and an interface unit 68 to provide interfacing between, amongst other things, the units 62, 64, 66 and an appropriately programmed computer 70. The computer 70 may be remote from the apparatus 10. However, in the preferred embodiment, the computer 70 is enclosed within the apparatus 10, advantageously in association with a display screen allowing measurement results to be displayed to the user. In either case, the computer 70 may communicate with the apparatus 10, or the relevant components thereof by any suitable conventional communications link. The interface unit 68 may include a digital-to-analogue converter (DAC) for interfacing between the computer 70 and the laser drive unit 62. The circuitry typically also includes a power supply conditioning unit 72 for conditioning the power supply (typically but not necessarily a mains supply) to the apparatus 10. The computer 70 may be configured for communication with remote devices (not shown) by one or more conventional communication links, e.g. an RS-232 link and/or an Ethernet connection. The processing and control circuitry may all be of conventional design and is not described further herein.

An overview of the typical operation of the apparatus 10 is now provided. In order to effect measurement of the oil content in the chamber 12, the computer 70 causes the laser 22 to be activated via the interface unit 68 (and in particular the DAC) and the laser drive unit 68. The laser 22 emits light 26 (usually modulated or otherwise controlled in conventional manner) through the measurement window 18 into the measurement chamber 12. Oil contained within the water in the chamber fluoresces in response to being excited by the laser light. The florescent light (indicated by arrows 27 in FIG. 1, which arrows also denote the line-of-sight of the light guide 28) is captured by the light guide 28 and transmitted therealong to the photosensor 30. The photosensor 30 transmits a corresponding electrical signal to the master circuit board 60. The signal is processed/conditioned by the processing/conditioning unit 66 and passed onto the DAC & PC Interface unit 68. The corresponding data from the unit 68 is transmitted to the computer 70, which, typically supports further processing software for, for example, analysing and/or processing the data received from the interface unit 68 in order that the desired information (typically including oil concentration levels) may be displayed (or communicated elsewhere).

The ultrasonic transducer 34 is used, as required, to clean the measurement window 18 and/or agitate or homogenise the water/oil in the chamber 12. The ultrasonic transducer 24 is driven by the piezo-electric transducers 42 which are energised by ultrasonic PSU 50. The ultrasonic PSU 50 is activated, or switched on and off, under the control of the computer 70 via the interface unit and control unit 64. The ultrasonic PSU 50 settings and calibration is conveniently managed by the computer 70 via a direct communication link, e.g. an RS-232 link. During use the ultrasonic vibrations imparted to the window 18, chamber 12 and the chamber contents serve to clean the window 18 and the chamber 12 as well as causing emulsification and homogenisation of the chamber contents.

In one mode of operation, measurement of the oil-in-water content may be made as the oil/water flows through the chamber 12. This allows continual monitoring of the oil-in-water content. This type of monitoring is useful for indicative trending of oil-in-water content, but is less useful for providing accurate measurements. In a second mode of operation, therefore, the apparatus 10 captures a liquid sample in the chamber 12 and performs measurement on the captured sample. To this end, at least the inlet 14 is associated with a respective valve (not shown in FIGS. 1 and 2) for sealing it from the inflow of liquid. In the preferred embodiment, the outlet 15 is higher, in use, than the chamber 12 and this allows a liquid sample to be retained in the chamber 12 without the need for a valve at the outlet 15. In alternative embodiments, however, the outlet 15 may be associated with a valve which may be operated as would be apparent to a skilled person to retain or release samples depending on the mode of operation. The operation of the valve may conveniently be controlled by a valve control unit 74 which in turn may be controlled by the computer 70 via the interface unit 68. When it is desired to take a measurement in the second mode of operation, the inlet valve is closed to capture an oil-in-water sample. Before measurement takes place, the sample is advantageously emulsified and homogenised by the ultrasonic transducer 34. After measurement is completed, the valve are opened and the sample is displaced by the flow of liquid into the chamber 12.

To facilitate the second mode of operation, it is preferred that the apparatus 10 is not connected directly in-line, i.e. in series, with the main pipe or conduit that carries the oil-in-water. Rather, it is preferred to connect the apparatus 10 in-line with a section of pipe or conduit that is in parallel with the main pipe or conduit. For example, the parallel section may comprise a pipe or conduit having both of its ends connected to the main pipe or conduit such that a portion of the contents of the main pipe/conduit flows along the parallel section. This allows the apparatus 10 to operate in the second mode of operation without appreciably interrupting the flow of oil-in-water in the main pipe.

Figure 3:
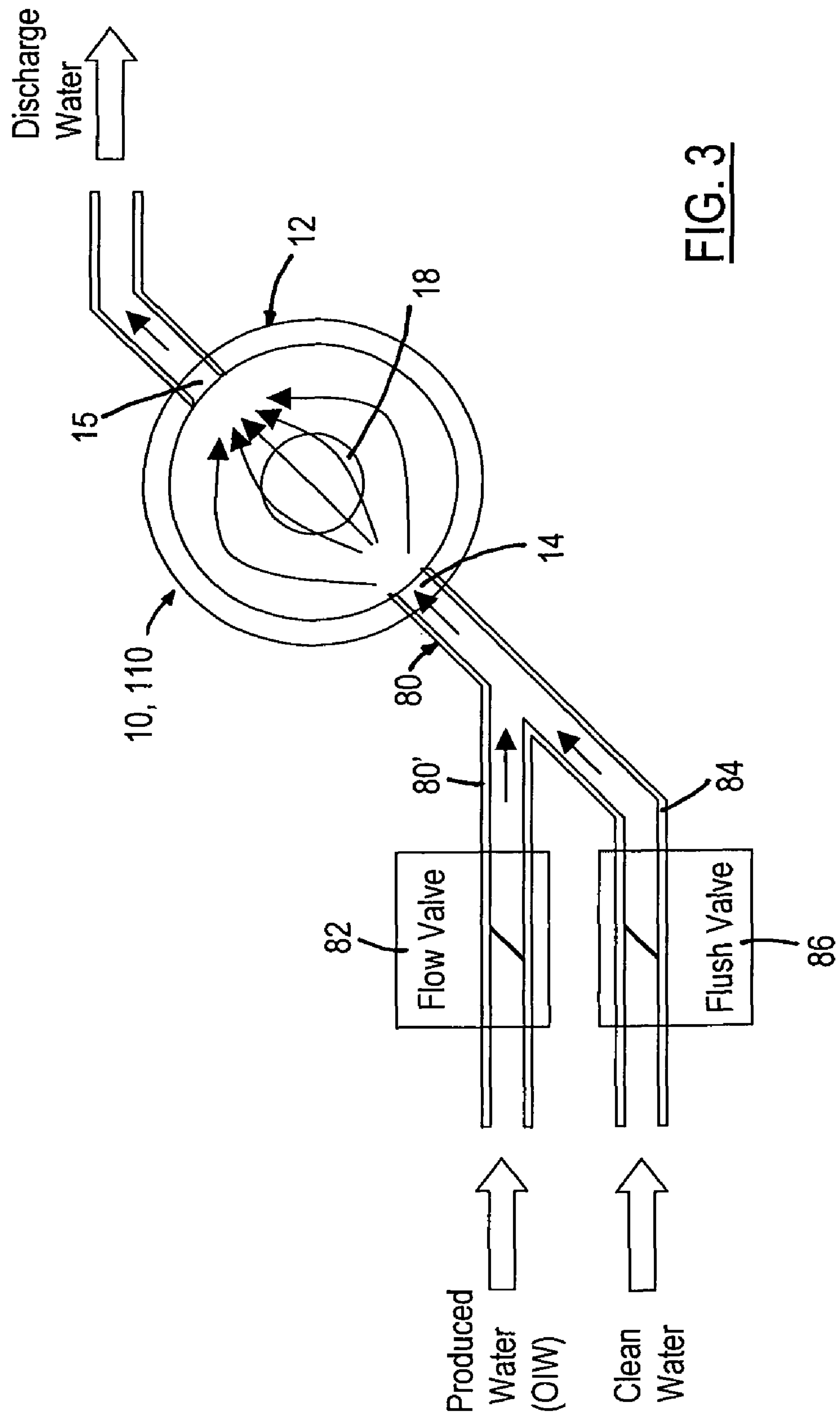
FIG. 3 is a schematic view of the apparatus of FIG. 1 or 2 shown in-line with a pipe or conduit.

Referring now in particular to FIG. 3, the apparatus 10 is shown connected in-line with a section of conduit 80. Typically, the conduit section 80 is in parallel with a main conduit (not shown). FIG. 3 illustrates a preferred embodiment which includes a flushing system for the chamber 12. During use, the oil-in-water reaches the inlet 14 of the chamber 12 via the conduit section 80' which may be opened or closed by flow valve 82 to allow, or to prevent, oil-in-water from flowing into the chamber 12. A second conduit section 84 is also in fluid communication with the inlet 14 of the chamber 12 and with a source of cleansing fluid, typically liquid, e.g. water. The second conduit section 84 is associated with a valve 86 which is operable to open or close the conduit section 84 thereby isolating the inlet 14 from the clean water source. The valves 82, 86 are conveniently operable under the control of the computer 70 via the valve control unit 74 (valve 1 and valve 2 in FIGS. 1 and 2). During use, the chamber 12 may be cleaned by closing valve 82 to cut off the supply of oil-in-water and opening valve 86. This causes the chamber 12 to be flushed with clean water (or any other suitable liquid). Valve 86 is closed after enough time has elapsed to allow the oil-in-water to be displaced from the chamber 12. The flushing process can be supplemented by ultrasonic action. The flushing operation may be an on-demand operation (e.g. user initiated), may be performed periodically and/or may be included as part of the measurement cycle.

Figure 5:
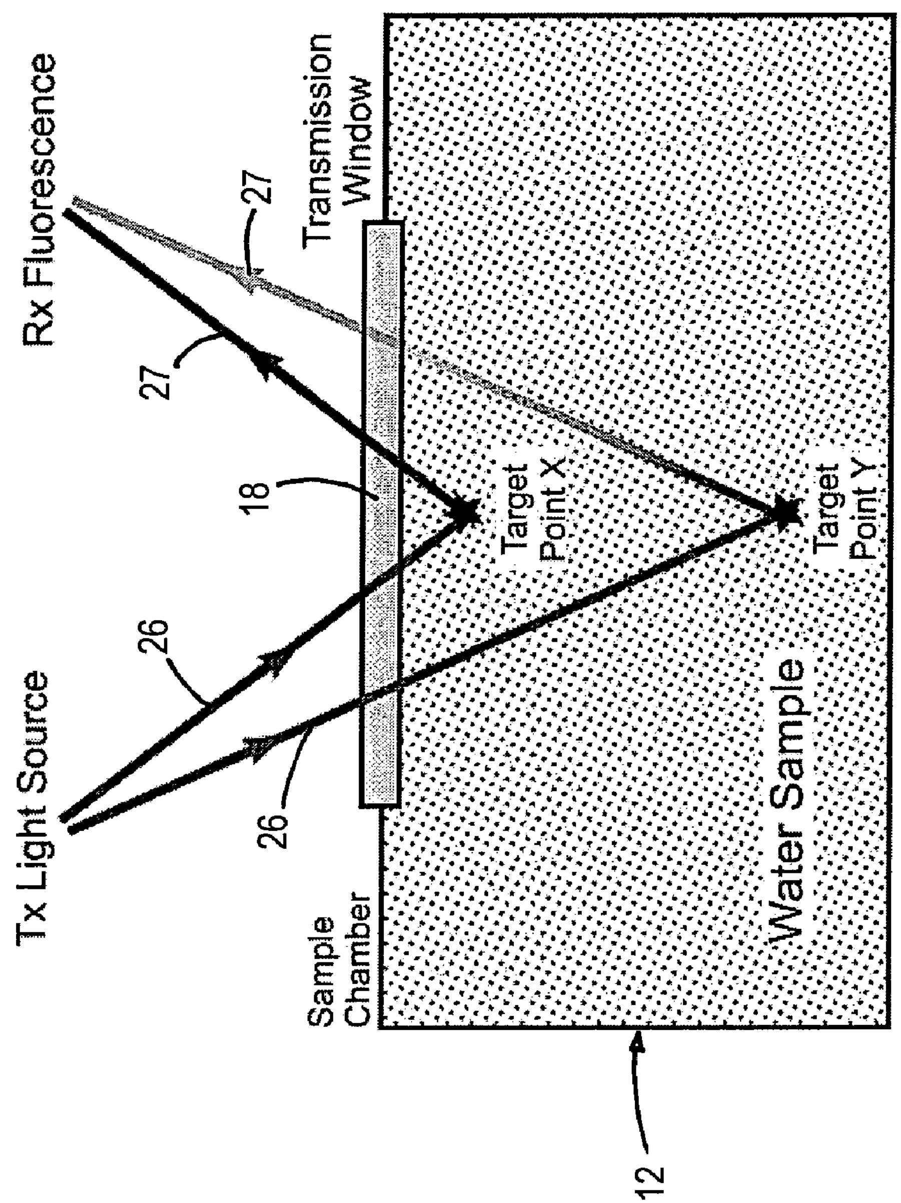
FIG. 5 is a schematic view of a measurement chamber associated with the apparatus of FIGS. 1 and 2 illustrating a preferred measurement technique.
Figure 6:
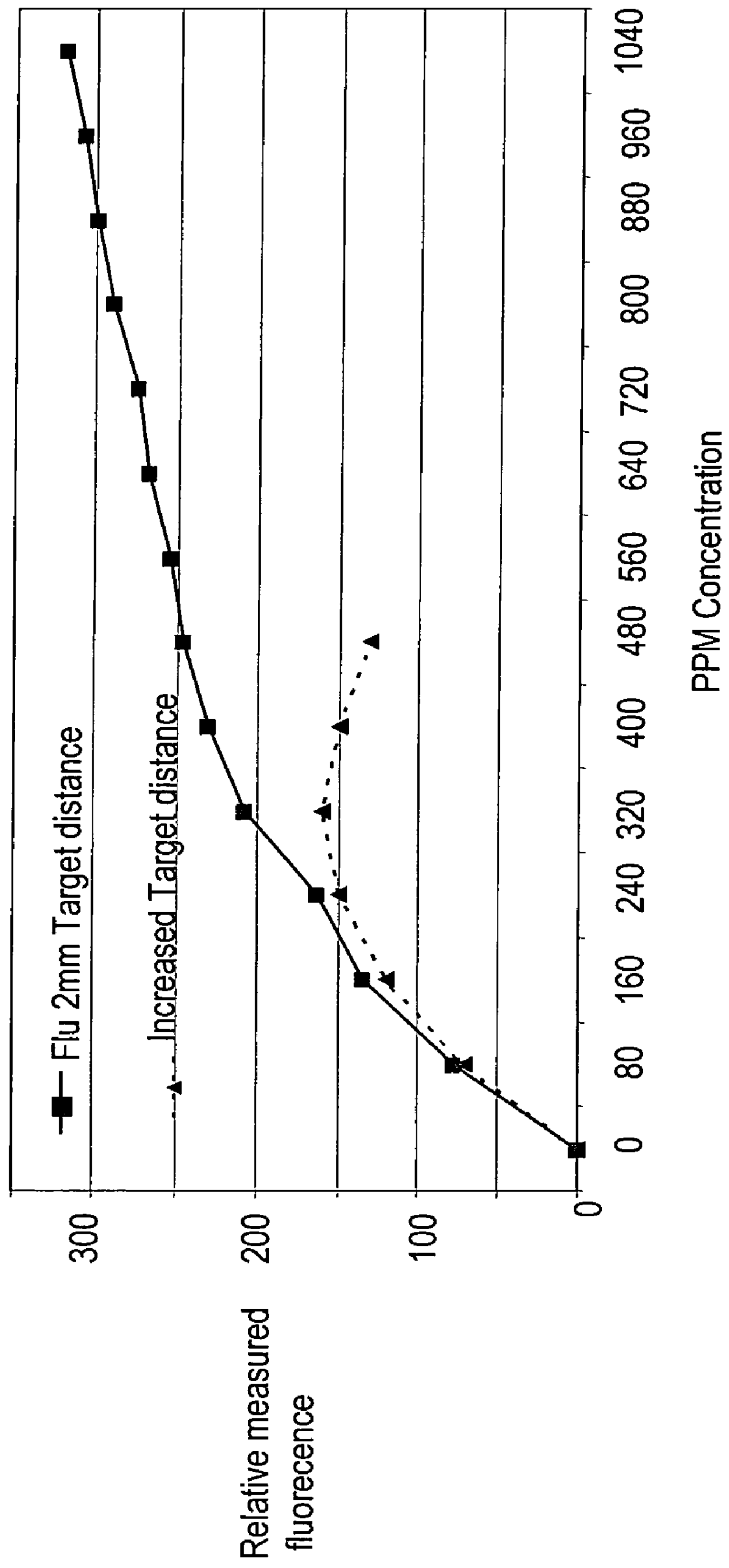
FIG. 6 is a graph showing oil particle concentration against measured fluorescence for different target distances from the measurement window.

Referring now to FIG. 5, a preferred arrangement of the excitation source and detector is described. The relative alignment of the optical transmitter, or excitation source (the laser 22 in the example of FIG. 1), and the portion (the light guide 28 in the example of FIG. 1) of the detector 24 that receives or gathers fluorescent light, defines a target region within the chamber 12 in which fluorescence is caused and detected. In particular, the target region is defined by the region in which the light signal 26 from the excitation source 22 intersects with the line-of-sight 27 of the detector 24. The target region may be said to be the region at which the excitation source and the receiver or detector are focussed. It is advantageous to arrange or align the excitation source 22 and light guide 28 (or other receiving component) such that the target region is as close to the measurement window 18 as possible, preferably at, or substantially at, the face of the window 18 within the chamber 12. In FIG. 5, a preferred target region or point X is shown close to the window 18. The shortest distance between the target point X and the face of the window 18 is preferably less than 10 mm, more preferably less than 5 mm. In the present example, the distance is approximately 2 mm. The line-of-sight 27 of the light guide 28 (or other receiver) typically has a breadth (e.g. depending on the number of optical fibres in the guide and on the breadth of each fibre) and so may advantageously be aligned to allow the collection of light emanating from a region beginning at, or substantially at, the face of the window 18. Advantageously, the region may extend into the chamber 12 by up to, say, 10 mm from the face of the window 18 (measured perpendicularly therefrom). Similarly, the light source 26 has a breadth depending on the characteristics of the excitation source 22. Hence, target point X may represent the centre point of the target region. By focussing the optical transmitter 22 and receiver 28 at or close to, and preferably within 2 mm of, the window 18, the effects of the turbidity of the oil-in-water on the transmission of light within the measurement chamber is reduced. If the distance from the window 18 to the sample target region is increased (see Target Point Y), turbidity will have a relatively greater attenuation on light transmission. As oil levels in the water increase, turbidity in the water increases proportionately, the turbidity will eventually critically attenuate the emitting fluorescent light within the measurement chamber, instead of the fluorescent levels increasing as oil concentration increases, the measured fluorescence falls. This is illustrated in FIG. 6 which illustrates the effects of the distance of the target region from the window 18 on the measured fluorescence (Y-axis) versus oil concentration (X-axis).

Figure 7:
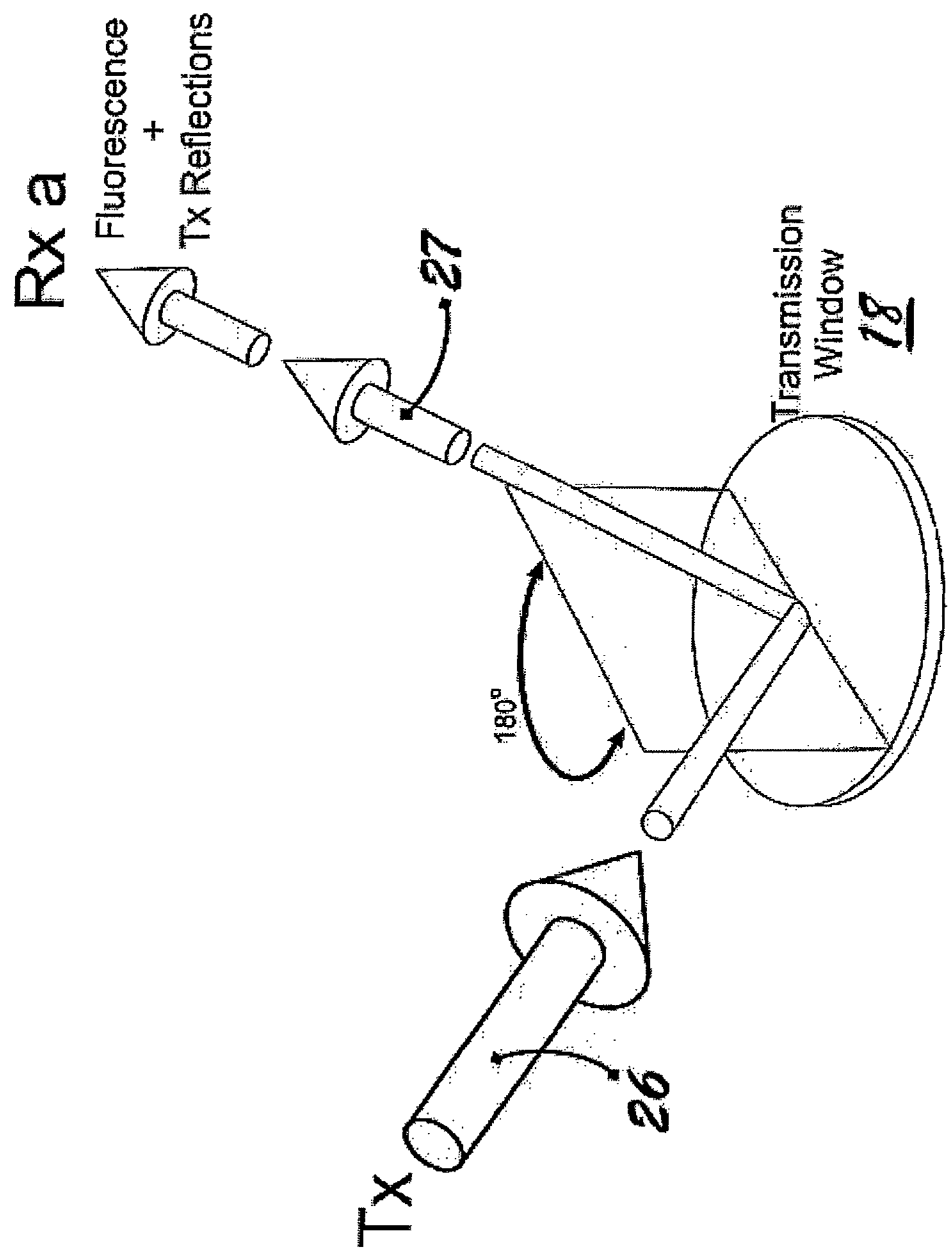
FIG. 7 illustrates a conventional spatial relationship between transmitted excitation light and received fluorescence.
Figure 8:
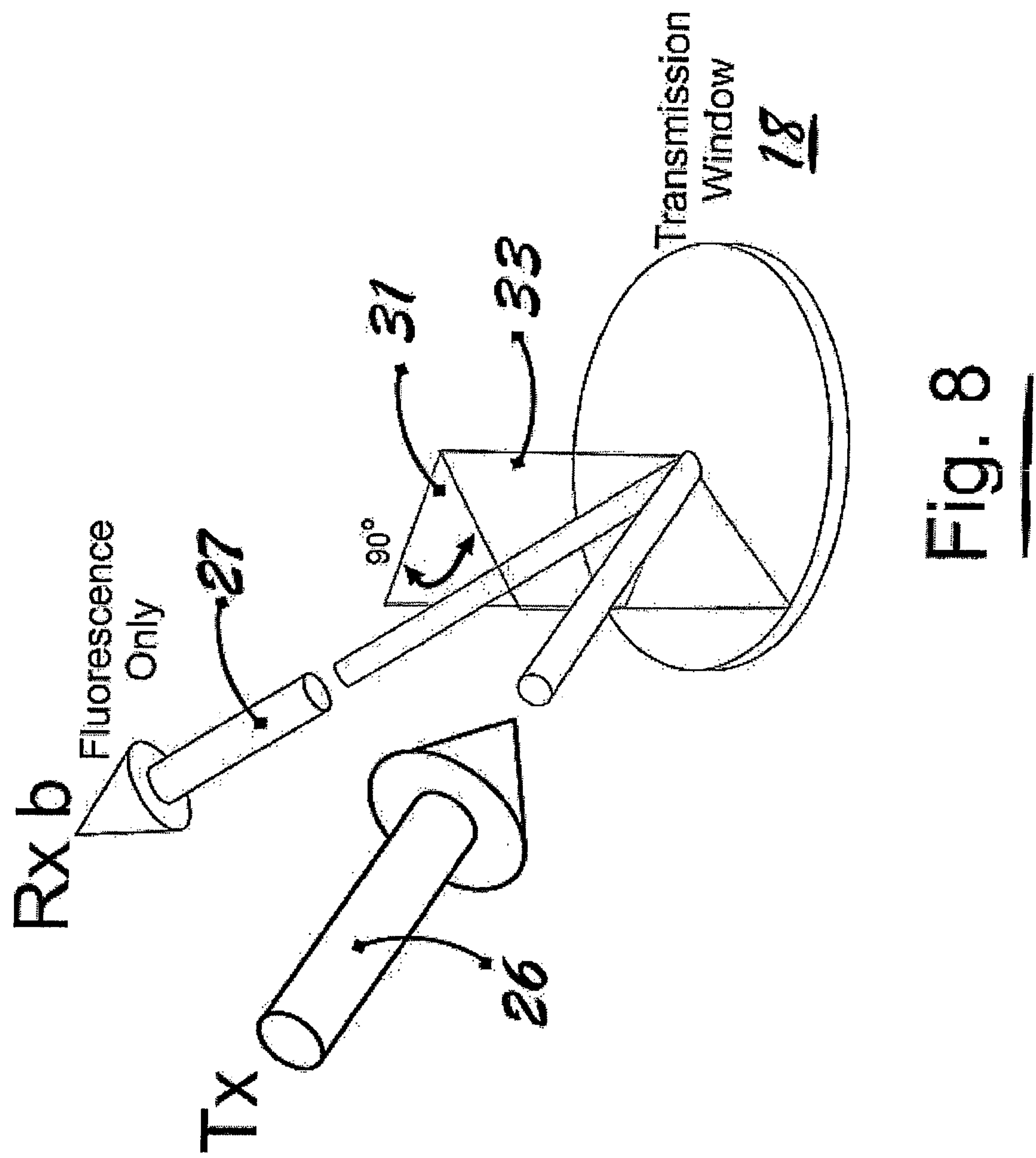
FIG. 8 illustrates a preferred spatial relationship between transmitted excitation light and received fluorescence in accordance with one aspect of the invention.

Referring now to FIGS. 7 and 8, a further advantageous aspect of the invention is described. FIG. 7 shows one possible arrangement of the transmitted excitation signal 26 and the line-of-sight 27 of the receiver (the latter also being the path traveled by the fluorescent light received by the receiver). The line-of-sight 27 and the signal 26 lie in the same plane taken perpendicularly to the surface of the window 18.

A limitation in conducting spectroscopy or optical analysis through a window is that reflections that are produced from the front and rear surfaces of the window. Optical filtering alone tends not to block these reflections sufficiently for them to have no impact on the measurement results. The reflections are at greatest intensity when the optical path RXa of the receiver is in the same plane as the optical path TX of the transmitter (taken perpendicularly to the face of the window).

To mitigate this problem, it is preferred to arrange the excitation source 22 and the receiver such that the line-of-sight 27 and the excitation signal 26 do not each lie in a common plane that is perpendicular, or substantially perpendicular, with the face of the window 18 (or to put this another way, the common plane of the line-of-sight 27 and the excitation signal 26 is not perpendicular with the face of the window 18). The preferred arrangement is illustrated in FIG. 8. The line-of-sight 27 (RXb) and the excitation signal 26 (TX) each lie in a respective plane 31, 33 that is perpendicular with the face of the window 18. These planes 31, 33 are non-coplanar with one another and, preferably, are substantially perpendicular with one another. As a result, reflection levels are reduced to insignificant levels that can be easily blocked to allow much lower levels of fluorescence to be detected.

In alternative embodiments (not illustrated), the apparatus 10 may include an optical spectrometer (not shown) in place of the photosensor module 30. Advantageously, the spectrometer is a broadband multi-wavelength spectrometer. In use, the spectrometer receives detected light signals via the light guide 28. The spectrometer may transmit corresponding measurement data to the computer 70, e.g. via an RS-232 or other suitable link, whereupon suitable computer software may process the data and display oil concentration levels to the user.

The invention is not limited to the embodiments described herein which may be modified or varied without departing from the scope of the invention.

The invention claimed is:

1. An apparatus for measuring the amount of fluorescent material in a liquid, the apparatus comprising a measurement chamber having a measurement window through which an excitation signal is transmitted and fluorescent light is detected, wherein the measurement window is a single component comprised of a single material and having a continuous inner face located within the measurement chamber through which both the excitation signal is transmitted and the fluorescent light is detected, and wherein the measurement window has a continuous outer face opposed to the inner face and located outside the measurement chamber and through which both the excitation signal is transmitted and the fluorescent light is detected, excitation means for generating said excitation signal and a detector for receiving said fluorescent light, wherein the apparatus further includes an ultrasonic transducer coupled to the measurement chamber and having at least one channel formed therein, said at least one channel opening onto said measurement window, wherein a light guide is at least partially inserted into said at least one channel, the light guide being arranged either to deliver the excitation signal into the chamber through the measurement window, or being arranged to carry fluorescent light from the chamber.

2. An apparatus as claimed in claim 1, wherein said at least one channel comprises a first channel associated with said excitation means and a second channel associated with said detector, wherein said light guide is at least partially inserted into said first channel and arranged to deliver the excitation signal into the chamber through the measurement window, and wherein another light guide is at least partially inserted into said second channel and being arranged to carry fluorescent light from the chamber to the detector.

3. An apparatus as claimed in claim 2, wherein said first and second channels converge in a direction towards the measurement window, the arrangement being such that the respective lines-of-sight of said excitation signal and of said another light guide intersect in said measurement chamber to define a target region from which fluorescent light may be detected.

4. An apparatus as claimed in claim 1, wherein said at least one channel comprises a first channel associated with said excitation means and a second channel associated with said detector, wherein said excitation means includes an excitation source at least partially inserted into said first channel and arranged to generate and direct the excitation signal into the chamber through the measurement window, and wherein said light guide is at least partially inserted into said second channel and being arranged to carry fluorescent light from the chamber to the detector.

5. An apparatus as claimed in claim 4, wherein said excitation source comprises a laser.

6. An apparatus as claimed in claim 1, in which the ultrasonic transducer includes a coupling mass portion held in contact with an outer face of the measurement window in order to impart ultrasonic vibrations thereto, wherein the excitation signal and fluorescent light is transmitted through the outer face of the measurement window, said coupling mass portion including a first portion and a second portion formed as separate components, said measurement window being held between the first and second portions which are secured together.

7. An apparatus as claimed in claim 1, in which the ultrasonic transducer includes a coupling mass portion held in contact with an outer face of the measurement window in order to impart ultrasonic vibrations thereto, wherein the excitation signal and fluorescent light is transmitted through the outer face of the measurement window, and wherein said at least one channel is formed in said coupling mass portion.

8. An apparatus as claimed in claim 7, in which the ultrasonic transducer includes a coupling mass portion held in contact with an outer face of the measurement window in order to impart ultrasonic vibrations thereto, wherein the excitation signal and fluorescent light is transmitted through the outer face of the measurement window, said coupling mass portion including a first portion and a second portion wherein the excitation signal and fluorescent light is transmitted through the outer face of the measurement window, said measurement window being held between the first and second portions which are secured together, and wherein said at least one channel is formed in said first portion of said coupling mass.

9. An apparatus as claimed in claim 8, wherein the second portion of the coupling mass forms at least part of a wall of the measuring chamber.

10. An apparatus as claimed in claim 1, wherein a protective sleeve is provided between said at least one channel and at least one of said light guide and said excitation source to protect the at least one of said light guide and said excitation source from the effects of ultrasonic vibration.

11. An apparatus as claimed in claim 1, in which the respective lines-of-sight of said excitation signal and of said light guide intersect in said measurement chamber to define a target region from which fluorescent light may be detected, and wherein said target region is located within the chamber substantially at said inner face.

12. An apparatus as claimed in claim 11, wherein the target region is centered at a point less than 10 mm of said inner face of the window.

13. An apparatus as claimed in claim 12, wherein the target region is centered at a point less than 5 mm of said inner face of the window.

14. An apparatus as claimed in claim 13, wherein the target region is centered at a point within 2 mm of said inner face of the window.

15. An apparatus as claimed in claim 1, wherein the excitation means and the detector are arranged such that the respective lines-of-sight of the detector and the excitation signal lie in a common plane which is not perpendicular with the inner face of the measurement window.

16. An apparatus as claimed in claim 15, wherein the arrangement is such that the respective lines-of-sight of the detector and of the excitation signal each lie in a respective plane that is perpendicular with the inner face of the window, said respective planes being substantially perpendicular with one another.

17. An apparatus as claimed in claim 1, further including a flushing system comprising a source of a cleaning fluid in fluid communication, during use, with an inlet to the measurement chamber; a valve provided between the fluid source and the inlet for controlling the flow of cleaning fluid to the chamber, the valve being operable to allow a quantity of cleaning liquid to flush the chamber.

18. An apparatus as claimed in claim 1, wherein both the inner and outer faces of the measurement window are located outside said at least one channel.

19. An apparatus as claimed in claim 1, wherein the inner and outer faces of the measurement window are parallel and spaced apart.

* * * * *